United States Patent [19]

Yoshimura et al.

[11] Patent Number: 5,066,747

[45] Date of Patent: * Nov. 19, 1991

[54] VINYL ETHERS AND FLUORINE-CONTAINING COPOLYMERS PREPARED THEREFROM

[75] Inventors: Tatsushiro Yoshimura; Nobuyuki Tomihashi; Tsutomu Terada, all of Takatsuki; Masayuki Yamana, Osaka; Kazuhiro Nakai; Takayuki Araki, both of Osaka, all of Japan

[73] Assignee: Daikin Industries, Ltd., Osaka, Japan

[*] Notice: The portion of the term of this patent subsequent to Aug. 28, 2007 has been disclaimed.

[21] Appl. No.: 588,872

[22] Filed: Sep. 27, 1990

Related U.S. Application Data

[62] Division of Ser. No. 168,073, Mar. 9, 1988, Pat. No. 4,970,331.

[30] Foreign Application Priority Data

| Mar. 10, 1987 | [JP] | Japan | 62-54690 |
| Jul. 29, 1987 | [JP] | Japan | 62-189590 |
| Jul. 29, 1987 | [JP] | Japan | 62-189591 |

[51] Int. Cl.$^5$ ............................................. C08F 12/20
[52] U.S. Cl. ..................................... 526/249; 526/250; 526/255; 526/293
[58] Field of Search ................. 526/249, 250, 255, 293

[56] References Cited

U.S. PATENT DOCUMENTS

| 2,514,895 | 7/1950 | Neher et al. |
| 2,524,921 | 10/1950 | Minter |
| 3,256,344 | 6/1966 | McTeer |
| 3,429,845 | 2/1969 | Bechtold et al. |
| 3,819,562 | 6/1974 | Cargagna |
| 4,015,057 | 3/1977 | Gall |
| 4,151,340 | 4/1979 | Ichimura et al. |
| 4,387,204 | 6/1983 | Zahir et al. |
| 4,579,924 | 4/1986 | Schwartz et al. | 526/245 |
| 4,611,087 | 9/1986 | Yamashita et al. |
| 4,705,887 | 11/1987 | Crivello |
| 4,749,807 | 6/1988 | Lapin et al. |
| 4,952,653 | 8/1990 | Tomihashi et al. | 526/249 |
| 4,970,331 | 11/1990 | Yoshimura et al. | 526/249 |

FOREIGN PATENT DOCUMENTS

| 0212508 | 3/1987 | European Pat. Off. | 526/249 |
| 0338498 | 10/1989 | European Pat. Off. | 526/249 |
| 62-169810 | 1/1986 | Japan |

*Primary Examiner*—Joseph L. Schofer
*Assistant Examiner*—N. Sarofima
*Attorney, Agent, or Firm*—Armstrong, Nikaido, Marmelstein, Kubovcik & Murray

[57] ABSTRACT

Vinyl ethers having a carboxyl group in a form of salt are stable and is usable as materials for fluorine-containing copolymers. The vinyl ethers can provide stable monomer compositions by mixing with vinyl ethers having a free carboxyl group when the former vinyl ethers are present in an amount of not less than 1% by mole of the latter vinyl ethers. The fluorine-containing copolymer prepared by copolymerizing fluoroolefins with the vinyl ethers are useful as aqueous coatings particularly electro dip coatings.

4 Claims, No Drawings

VINYL ETHERS AND FLUORINE-CONTAINING COPOLYMERS PREPARED THEREFROM

This is a division of application Ser. No. 168,073 filed Mar. 9, 1988 now U.S. Pat. No. 4,970,331.

BACKGROUND OF THE INVENTION

The present invention relates to novel vinyl ethers having a carboxylic acid salt, and relates to compositions containing the vinyl ethers, and further relates to fluorine-containing copolymers prepared therefrom, which are useful for materials of fluorine resin paints.

Fluorine resins having a carboxyl group can be prepared by copolymerizing vinyl ethers having a carboxyl group and fluoroolefins. However, synthesis of vinyl ethers having a carboxyl group is very difficult. For example, an attempt to synthesize vinyl ethers having a carboxyl group by reacting hydroxyalkyl vinyl ethers with dibasic acid anhydrides (half-esterification) results in failure, because the carboxyl group of the product immediately reacts with the vinyl group of the same product to form a ring.

Therefore, fluorine-containing copolymers having carboxyl groups may be, for example, prepared by copolymerizing fluoroolefins and vinyl ethers having a hydroxyl group, and then reacting the hydroxyl groups in the copolymer with dibasic acid anhydrides (half-esterification) (c.f. Japanese Tokkyo Kokoku No. 49323/1986). The process, however, has a defect that since the half-esterification must be carried out after copolymerization, cheap alcohols which react with the dibasic acid anhydrides cannot be used as solvents in the copolymerization.

As a result of the present inventors, intensive study for preparation of vinyl ethers having a carboxyl group, it has been found out the facts that the intramolecular ring closure reaction does not happen when hydroxyalkyl vinyl ethers are reacted with dibasic acid anhydrides in the presence of basic compounds, and that stability of the resulting vinyl ethers can be improved in the form of carboxyl salts with the basic compounds, and also that yield of copolymerization with fluoroolefins can be remarkably increased, and then the present invention has been completed.

SUMMARY OF THE INVENTION

The present invention relates to vinyl ethers (I) having a carboxyl group in the form of salt represented by the formula (I):

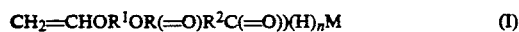

CH$_2$=CHOR$^1$OR(=O)R$^2$C(=O))(H)$_n$M     (I)

wherein R$^1$ is a divalent aliphatic residue of 2 to 10 carbon atoms, R$^2$ is a divalent organic residue, and M is an alkali metal, or a mono-functional basic compound which contains nitrogen atom or phosphorus atom and has a pKa of 6 to 12, and n is 0 when M is the alkali metal and is 1 when M is other.

The present invention also relates to monomer compositions which comprise the vinyl ethers (I) and vinyl ethers having a free carboxyl group represented by the formula (II):

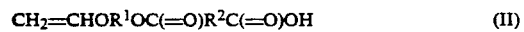

CH$_2$=CHOR$^1$OC(=O)R$^2$C(=O)OH     (II)

wherein R$^1$ and R$^2$ are as defined above, and contain the vinyl ethers (I) in an amount of not less than 1% by mole of the vinyl ethers (II).

The present invention further relates to fluorine-containing copolymers prepared by copolymerizing fluoroolefins and the vinyl ethers (I) or the monomer compositions.

DETAILED DESCRIPTION

The reason why the vinyl ethers (I) would not form a ring is assumed as follows:

The vinyl ethers (II) having a free carboxyl group have a cationic reactivity and forms a ring due to action of H$^\oplus$ yielded from the carboxyl group, according to the following reaction scheme.

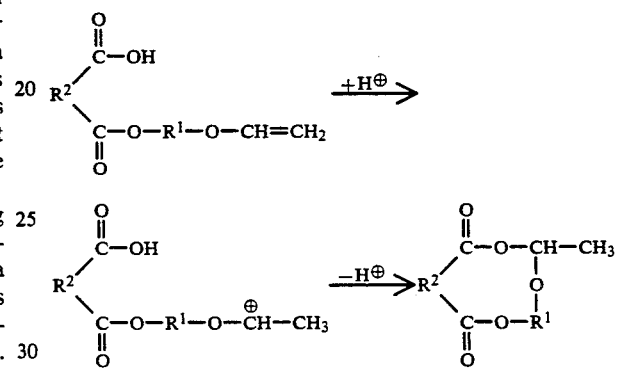

However, the vinyl ethers (I) having a carboxyl group in the form of salt are stable in the following state:

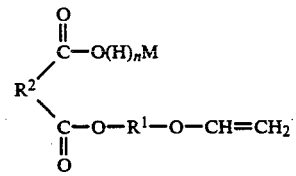

wherein R$^1$, R$^2$, M and n are as defined above.

The reason why the mixture of the vinyl ethers (I) and (II) is stable when the vinyl ethers (I) is present in an amount of not less than 1% by mole of the vinyl ethers (II) is assumed that a concentration of H$^\oplus$ in the mixture is reduced due to buffer effect of the vinyl ethers (I).

The vinyl ethers (I) of the present invention can be prepared by reaction hydroxyalkyl vinyl ethers represented by the formula:

CH$_2$=CHOR$^1$OH wherein R$^1$ is as defined above, dibasic acid anhydrides represented by the formula:

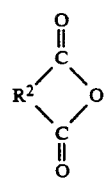

wherein R² is as defined above, and alkali metal compounds or mono-functional basic compounds which contain nitrogen atom or phosphorus atom and has a pKa (acid dissociation constant in water at 25° C.) of 6 to 12 (hereinafter referred to as "base" when the two compounds are not distinguished).

Examples of the hydroxyalkyl vinyl ethers are, for instance, 4-hydroxybutyl vinyl ether, 2-hydroxyethyl vinyl ether, 3-hydroxy-n-propyl vinyl ether, 2-hydroxyisopropyl vinyl ether, 2-hydroxy-2-methylethyl vinyl ether, 2-hydroxy-1,1-dimethylethyl vinyl ether, 4-hydroxycyclohexyl vinyl ether, 3-hydroxycyclohexyl vinyl ether, 2-hydroxycyclohexyl vinyl ether, 4-hydroxybenzoxy vinyl, and the like.

Examples of the substituent R² which is contained in the dibasic acid anhydrides and the vinyl ethers (I) or (II) are, for instance, residues represented by the formula (i):

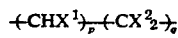  (i)

wherein X¹ is hydrogen atom or an alkyl group of 1 to 3 carbon atoms, X² is hydrogen atom or an alkyl group of 1 to 3 carbon atoms, and p and q are 0 or an integer of 1 to 11, provided that they are not 0 at the same time; residues represented by the formula (ii):

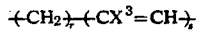  (ii)

wherein X³ is hydrogen atom or an alkyl group of 1 to 3 carbon atoms, r is 0 or an integar of 1 to 3, and s is an integar of 1 to 3; residues represented by the formula (iii):

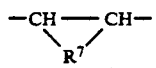  (iii)

wherein R⁸ is $-(CHX^5)_u-$ in which X⁵ is hydrogen atom or an alkyl group of 1 or 3 carbon atoms and u is an integar

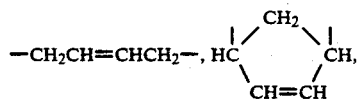

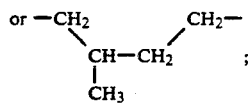

residues represented by the formula (iv):

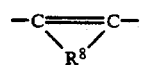  (iv)

wherein R⁸ is $-(CHX^5)_u-$ in which X⁵ is hydrogen atom or an alkyl group of 1 or 3 carbon atoms and u is an integar of 3 to 4, or $-(CX^6=CX^7)_v-$ in which X⁶ and X⁷ are the same or different and each is hydrogen atom or an alkyl group of 1 to 3 carbon atoms and v is an integar of 2 to 3;

residues represented by the formula (v):

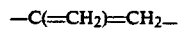  (v);

residues represented by the formula (vi):

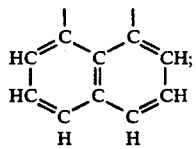  (vi)

and the like.

Examples of the dibasic acid anhydrides are, for instance, maleic anhydride, succinic anhydride, methylsuccinic anhydride, phthalic anhydride, adipic anhydride, glutaric anhydride, glutaconic anhydride, itaconic anhydride, 1,8-naphthalic anhydride, citraconic anhydride, 1,2-cyclohexanedicarboxylic anhydride, 4-methyl-1,2-hexanedicarboxylic anhydride, cis-4-cyclohexene-1,2-dicarboxylic anhydride, 1-cyclohexene-1,2-dicarboxylic anhydride, an addition product prepared by Diels-Alder reaction of cyclopentadiene and maleic anhydride, and the like.

Generally a reaction of hydroxyl compounds and dibasic acid anhydrides proceeds in the presence of basic catalysts according to the following scheme.

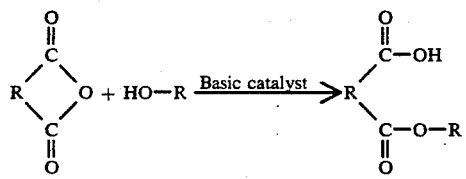

In this reaction, in order to obtain the desired product in a yield of more than 90%, enough amount of the basic catalyst to be used is at most 0.5% by mole of the dibasic acid anhydrides. According to the present inventors research, however, when hydroxyvinyl ethers having a high cationic reactivity are used as the hydroxyl compounds, the desired reaction products cannot be obtained in the absence of basic compound, as described hereinafter. Further, if the amount of the basic compound is about 0.5% by mole, not only the yield of the desired product becomes lower, but also the stability of the product is bad. Accordingly, the resulting products are not suitable to monomers for polymerization.

However, when the bases ③ are used in an amount of not less than 1% by mole of the dibasic acid anhydrides ②, a yield becomes higher than 90% and, also since the resulting reaction mixture is stable, reduction of an effective yield can be prevented. The reason is assumed that the bases ③ prevent a reaction between the carboxyl group and the vinyl group and also prevent the obtained vinyl ethers (II) from the formation of intramolecular ring. The bases ③ can be stoichiometrically reacted with the carboxyl group. The bases ③ are present in the reaction system at an amount of not less than 1% by mole of the acid anhydrides ②, and in such a case the resulting reaction product is a mixture of the vinyl ethers (I) and (II).

The vinyl ethers (I) of the present invention can be prepared by adding the bases ③ to the mixture of the vinyl ethers (I) and (II), and reacting the bases ③ with the vinyl ethers(II). The bases ③ added after the half-esterification are the same as or different from the bases ③ used in the half-esterification. In this case the bases ③ can be stoichiometrically reacted with the carboxyl group of the vinyl ethers (II).

As the bases ③, the alkali metal compounds and the above-mentioned particular mono-functional basic compounds are used.

Preferable alkali metal compounds are compounds of Li, K or Na, and examples thereof are, for instance lithium hydroxide, sodium hydroxide, potassium hydroxide, lithium carbonate, sodium carbonate, potassium carbonate, sodium methylate, sodium ethylate, potassium methylate, and the like.

The particular mono-functional basic compounds are mono-functional basic compounds which contain nitrogen atom or phosphorus atom and have a pKa of 6 to 12, preferably 8 to 11. The basic compounds having a pKa of the range have an ability to form salts, and have a high stabilizing property to stabilize the vinyl ethers (II). Namely, basic compounds having a pKa higher than that of the carboxylic acids of the dibasic acid anhydrides have a high salt-forming ability. Preferable basic compounds have a pKa higher than that of the carboxylic acids to be reacted by 3 to 8. Suitable examples of the particular mono-functional basic compounds are ammonia, amines, phosphines, and the like. Particularly tertiary amines are preferable.

Examples of the amines are, for instance, methylamine, ethylamine, n-propylamine, isopropylamine, n-butylamine, isobutylamine, sec-butylamine, 1,2-dimethylpropylamine, 2-ethylhexylamine, tridecylamine, dimethylamine, diethylamine, di-n-propylamine, diisopropylamine, dibutylamine, diisobutylamine, di-sec-butylamine, di-2-ethylhexylamine, trimethylamine, triethylamine, tri-n-propylamine, tri-n-butylamine, N-methylbutylamine, N-ethylbutylamine, N, N-dimethylethylamine, N, N-dimethyloctadecylamine, 2methoxyethylamine, 3-ethoxyethylamine, cyclohexylamine, N, N-dimethylcyclohexylamine, dicyclohexylamine, benzylamine, N, N-dimethylbenzylamine, 4-methoxyphenylethylamine, ethanolamine, diethanolamine, triethanolamine, isopropanolamine, pyrrolidine, piperidine, 1-methylpiperidine, 4-methylpiperidine, morpholine, and the like.

Examples of the phosphines are, for instance, di-or tri-alkylphosphines such as trimethylphosphine, triethylphosphine, tripropylphosphine, tributylphosphine, trioctylphosphine, trilaurylphosphine, tristearylphosphine, dimethylphosphine, diethylphosphine, dibutylphosphine, dioctylphosphine or dilaurylphosphine; di-or tri-substituted alkylphosphines such as tris(3-hydroxypropyl)phosphine, tris(2-cyanoethyl)phosphine, tris(2-methoxyethyl)phosphine, tris(2-chloroethyl)phosphine, tris(2-methoxycarbonyl)phosphine, tris[2-(2-dimethylaminoethoxy)carbonyl)]phosphine, tris(2-ethoxycarbonyl)phosphine, bis(3-hydroxypropyl)phosphine or bis(2-cyanoethyl)phosphine; alicyclic phosphines such as dicyclopentylphosphine, dicyclohexylphosphine, tricyclopentylphosphine or tricyclohexylphosphine; di-or tri-arylphosphines such as triphenylphosphine, tri(4-methylphenyl)phosphine, disphenylphosphine or bis(4-methylphenyl)phosphine; di-or tri-aralkylphosphines such as tribenzylphosphine, triphenetylphosphine, dibenzylphosphine or diphenetylphosphine; phosphines containing phosphorus atom in a ring such as tetramethylenephosphine or tetramethylene-methylphosphine; phosphines in which two or three different organic residues are bonded to phosphorus atom such as diphenylmethylphosphine, diphenylethylphosphine or phenyldiethylphosphine; and the like. Particularly tributylphosphine and triphenylphosphine are preferable.

The reaction temperature is generally −80° to 100° C., preferably 0° to 50° C. Reaction solvents may be generally used, but may not be used. There may be used solvents excepting alcohols which are reactive to the dibasic acid anhydrides. Preferred solvents are ketones such as acetone, methyl ethyl ketone and methyl isobutyl ketone, because they do not cause the decrease of reactivity of the starting materials and also the coloring of the reaction products. The bases ',crc/3/ may generally be used in a molar ratio of 0.01 to 1.2 to the dibasic acid anhydrides ②, preferably 0.05 to 1.0.

The present invention can provide stable monomer compositions comprising the vinyl ethers (I) and the vinyl ethers (II). As mentioned above, since the vinyl ethers (II) are very unstable and immediately form the intramolecular ring, the vinyl ethers (II) have problems as to a stability, particularly storage stability when using as a monomer. According to the present invention, a storage stability of the vinyl ethers (II) can be remarkably enhanced in the presence of the vinyl ethers (I) in an amount of not less than 1% by mole of the vinyl ethers (II), preferably not less than 5 by mole.

The monomer compositions may be obtained as the reaction products according to the preparation of the vinyl ethers (I), or may be obtained by adding the bases ③ to the reaction products Further, the present invention relates to fluorine containing copolymers obtained by copolymerizing fluoroolefins with the vinyl ethers (I) or the monomer compositions of the vinyl ethers (I) and (II).

Examples of the fluoroolefins are, for instance, tetrafluoroethylene, chlorotrifluoroethylene, hexafluoropropylene, trifluoroethylene, vinylidene fluoride, vinyl fluoride, and the like.

In the present invention, a reaction molar ratio of the vinyl ethers (I) or (I) and (II)/the fluoroolefins is generally 0.1–80/20–99.9.

The fluorine-containing copolymers preferably contain, when using as aqueous paints, the vinyl ethers (I) or (I) and (II) in an amount of 5 to 60% by mole for improving a water-solubility of the copolymer. Particularly for electro dip coatings, not less than 30% of the carboxyl group of the vinyl ethers is neutralized. As the neutralizing agents, the above-mentioned basic compounds 3 may be used.

When using the fluorine-containing copolymers as organic solutions, i.e. organic solvent type paints, a content of the vinyl ethers (I) or (I) and (II) is preferably 1 to 15% by mole in view of adhesive property to substrates, and preferably 2 to 10% by mole in view of dispersibility of pigments.

The fluorine-containing copolymers may contain various ethylenic unsaturated compounds in an amount of not more than 80% by mole of the copolymer, in addition to the vinyl ethers and the fluoroolefins. Examples of the copolymerizable ethylenic unsaturated compounds are, for instance, an alkyl vinyl ether or vinyl ester represented by the formula:

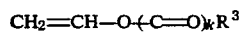

wherein $R^3$ is an aliphatic residue of 1 to 17 carbon atoms, an alicyclic residue of 3 to 17 carbon atoms, a fluoroalkyl residue of 1 to 20 carbon atoms, a hydroxyl-containing aliphatic residue of 1 to 17 carbon atoms, a hydroxyl-containing alicyclic residue of 3 to 17 carbon atoms or a hydroxyl-containing aromatic residue of 6 to 20 carbon atoms, and k is 0 or 1. Examples are, for instance, methyl vinyl ether, ethyl vinyl ether, n-propyl vinyl ether, isopropyl vinyl ether, n-butyl vinyl ether, isobutyl vinyl ether, t-butyl ether, n-pentyl vinyl ether, n-hexyl vinyl ether, n-octyl vinyl ether, 2-ethylhexyl vinyl ether, cyclohexyl vinyl ether, lauryl vinyl ether, stearyl vinyl ether, 2,2,2-trifluoroethyl vinyl ether, 2,2,3,3-tetrafluoropropyl vinyl ether, 2,2,3,3,3-pentafluoropropyl vinyl ether, 2,2,3,3,4,4,5,5-hephafluorobutyl vinyl ether, vinyl acetate, vinyl propyonate, vinyl butyrate, vinyl pivalate, vinyl caproate, vinyl laurate, vinyl lauroate, vinyl Versalate ®, vinyl cyclohexancarboxylate, 4-hydroxylbutyl vinyl ether, 2-hydroxyethyl vinyl ether, 3-hydroxy-n-propyl vinyl ether, 2-hydroxyisopropyl vinyl ether, 2-hydroxy-2-methylethyl vinyl ether, 2-hydroxy-1,1dimethylethyl vinyl ether, 4-hydroxycyclohexyl vinyl ether, 3-hydroxycyclohexyl vinyl ether, 2-hydroxycyclohexyl vinyl ether, 4-hydroxylbenzoxy vinyl, and the like.

Further a compound represented by the following formula may be used.

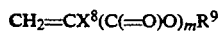

wherein $X^8$ is hydrogen atom, chlorine atom, fluorine atom, methyl or trifluoromethyl, $R^9$ is hydrogen atom, chlorine atom, an aliphatic residue of 1 to 17 carbon atoms, a hydroxyl-containing aliphatic residue of 1 to 17 carbon atoms, an alicyclic residue of 3 to 17 carbon atoms or a fluoroalkyl residue of 1 to 20 carbon atoms, and m is 0 or 1. Examples are, for instance, ethylene, propylene, 1-butene, isobutene, styrene, vinyl chloride, vinylidene chloride, isobutyl acrylate, methyl acrylate, ethyl methacrylate, 2,2,3,3,3-pentafluoropropyl α-fluoroacrylate, 2,2,3,3,4,4,5,5,6,6,7,7-dodecafluoropentyl ° -trifluoromethylacrylate, 2-hydroxyethyl methacrylate, cyclohexyl acrylate, 2,2,3,3,4,4,5,5,6,6,7,7,8,8,9,9,10,10,11,11,12,12,13,13,1 4,14,15,15,15-nonacosafluoropentadecyl acrylate, 2-hyeroxypropyl α-hyeroxypropyl α-chloracrylate, octyl α-chloroacrylate, octadecyl acrylate, and the like.

In addition, a compound represented by the formula:

wherein $X^9$ is chlorine atom, hydroxylgroup or an alkyloxy group of 1 to 8 carbon atoms, may also be used. Examples are, for instance, allylalcohol, allylchloride, allyl methyl ether, allyl isopropyl ether, allyl octyl ether, and the like.

If necessary, a small amount of divinyl ethers or trivinyl ethers which are salts of the vinyl ethers (II) with polyvalent metals (e.g. Mg, Ca, Zn or Al) or polyfunctional compounds containing nitrogen atom or phosphorus atom (e.g. polyamines such as alkyldiamines or alkyltriamines, polyphosphines such as alkydiphosphines or alkyltriphosphines), may be present n the copolymerization system as copolymerizabhle monomers. In this case, the reaction products are partially gelled and be useful for matting agents.

The copolymerization may be carried out by emulsion polymerization or dispersion polymerization. In the both polymerizations, a polymerization temperature is generally −20° to 150° C., preferably 5° to 95° C. which may be optionally changed depending with a kind of an initiating agent or solvent. Also a reaction pressure may be optionally selected, and is generally 0 to 50 kg/cm²G. Examples of polymerization solvents are, for instance, halogenated hydrocarbons such as trichlorotrifluoroethane and dichlorotetrafluoroethane; ketones such as acetone, methyl ethyl ketone and methyl isobutyl ketone; esters such as ethyl acetate and butyl acetate; aromatic hydrocarbons such as toluene and xylene; alcohols such as methanol, ethanol, propanol and butanol; glycol ethers such as ethyl cellosolve, butyl cellosolve, monoglyme and diglyme; water; and the like.

Examples of the initiating agents are, for instance, persulfates such as ammonium persulfate and potassium persulfate; redox type initiating agents comprising persulfates and sulfites (e.g. potassium sulfite, sodium sulfite or the like) and acid sulfites (e.g. acid potassium sulfite, acid sodium sulfite or the like); organic peroxides such as diisopropyl peroxydicarbonate, tert-butyl peroxybutyrate, benzoyl peroxide and isobutyryl peroxide; azo compounds such as azoisobutylonitrile; and the like. The initiating agents may be generally used in an amount of 0.001 to 5% by weight of the total weight of the monomers, preferably 0.05 to 2.0% by weight.

The copolymerization process can be carried out batchwise, semi-continuously or continuously without any limitaion.

As described above, since the vinyl ethers (I) which contain the salt of carboxyl group have the same reactivity as of usual vinyl ethers and are copolymerizable with the other ethylenic unsaturated compounds such as fluoroolefins, vinyl esters or vinyl ethers, the vinyl ethers (I) can provide copolymers having carboxyl groups. The resulting copolymers are excellent in a hydrophilic property, a dispersibility of pigments and an adhesive property, and thus can be utilized as materials for aqueous coatings, electro dip coatings, and the like.

According to the vinyl ethers (I) and the monomer compositions containing thereof, the intramorecular ring formation of the vinyl ethers (II) having a free carboxyl group can be prevented, and the stability of the vinyl ethers (II) can be improved, and thus are useful as monomers for the above polymerization.

The fluorine-containing copolymers of the present invention can be prepared in a non-restricted solvent system. The fluorine-containing copolymers contain carboxyl groups uniformly, which can provide excellent paints.

The present invention is more particularly described and explained by means of the following Examples. It is to be understood that the present invention is not limited to the Examples, and various changes and modifications may be made in the invention without departing from the spirit and scope thereof.

EXAMPLE 1

A flask of 1000 ml was charged with 154 g (1.0 mole) of 1,2-cyclohexanedicarboxylic anhydride (as an acid anhydride) and 40 g of acetone, and then 101 g (1.0 mole) of triethylamine (as a base) was added thereto. The mixture was stirred for 5 minutes with a magnetic stirrer.

To the mixture was added dropwise 116 g (1.0 mole) of hydroxybutyl vinyl ether at a rate of 2 g/min. while keeping the mixture at 0° to 10° C. by cooling with ice water.

The resulting reaction mixture was subjected to Fourier transform nuclear magnetic resonance analysis (FT-NMR, $^{13}C$, tetramethylsilane standard). As a result, it was comfirmed that the vinyl ether (I) of the invention having the following formula was yielded in approximately 100%. The data of chemical shifts of each carbon atoms (designated by a to m) are shown in the followings.

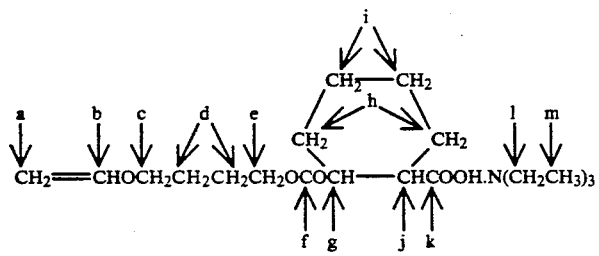

δ(ppm)=85.6 (a), 151.5 (b), 67.2 (c), 25.3–25.6 (d), 62.8 (e), 173.3 (f), 42.9 (g), 27.4 (h), 24.4 (i), 43.5 (j), 176.2 (k), 44.9 (l), 9.1 (m)

EXAMPLES 2 TO 5

The same procedures as in Example 1 were repeated except that the following acid anhydrides were used instead of 1,2-cyclohexanedicarboxylic anhydride to give the vinyl ethers (I) of the invention. The data of the FT-NMR analysis are noted together.

Examples 2

Acid anhydride: Maleic anhydride (98.0 g=1.0 mole) Vinyl ether (I) of the invention:

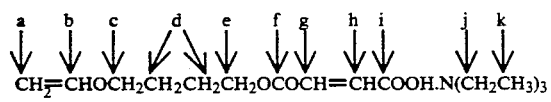

δ(ppm)=86.1 (a), 152.2 (b), 67.7 (c), 26.2–29.8 (d), 63.2 (e), 168.5 (f), 136.2 (g), 141.2 (h), 171.0 (i), 46 1 (j), 10.0 (k).

Yield: 100%

Example 3 Acid anhydride: Succinic anhydride (100.0 g=1.0 mole) Vinyl ether (I) of the invention:

δ(ppm)=86.2 (a), 152.2 (b), 67.7 (c), 25.8–26.1 (d), 63.8 (e), 172.8 (f), 31.2 (g), 175.7 (h), 45.7 (i), 9.8 (j).
Yield: 100%

Example 4

Acid Anhydride: Addition product obtained by Diels-Alder reaction of maleic anhydride and cyclopentadiene (164.0 g=1.0 mole). Vinyl ether (I) of the invention:

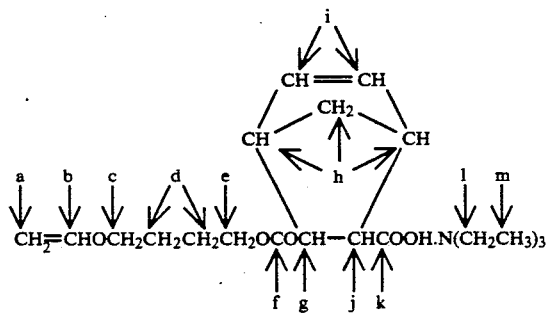

δ(ppm)=86.1 (a), 152.2 (b), 67.8 (c), 25.7–26.3 (d), 63.3 (e), 172.8 (f), 46.4–50.6 (g,h,j), 134.4–135.0 (i), 175.1 (k), 45.6 (l), 10.1 (m).

Yield: 100%,

Example 5

Acid anhydride: 4-methyl-1,2-cyclohexanedicarboxylic anhydride (168.0 g=1.0 mole) Vinyl ether (I) of the invention:

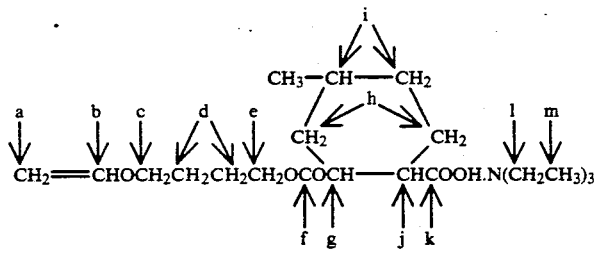

δ(ppm)=85.8 (a), 151.9 (b), 67.4 (c), 25.6–26.0 (d), 63.0 (e), 176.3 (f), 22.7–33.1 (g,h,i,j), 173.5 (k), 45.2 (l), 9.4 (m).

Yield: 100%

EXAMPLES 6 TO 8

The same procedures as in Example 1 were repeated except that the following bases were used instead of triethylamine to give the vinyl ethers (I) of the invention. The data of the FT-NMR analysis are noted together.

Example 6

Base: N-dimethylbenzylamine (135 g=1.0 mole) Vinyl ether (I) of the invention:

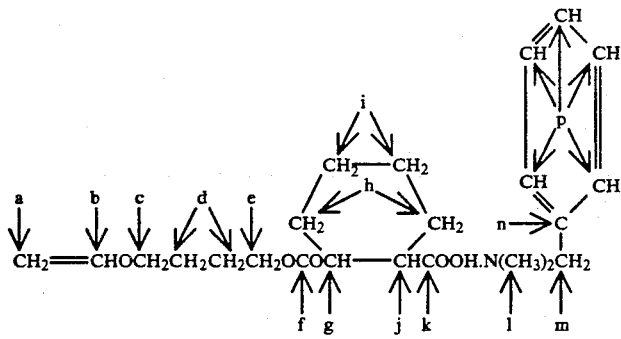

δ(ppm)=86.1 (a), 151.8 (b), 67.4 (c), 25.7-25.9 (d), 63.4 (e), 173.5 (f), 43.6 (g), 27.6 (h), 24.2-24.7 (i), 43.6 (j), 176.7 (k), 43.1 (l), 62.1 (m), 135.4 (n), 127.9-130.1 (p).
Yield: 100%

Example 7

Base: Tributylamine (185 g=1.0 mole) Vinyl ether (I) of the invention:

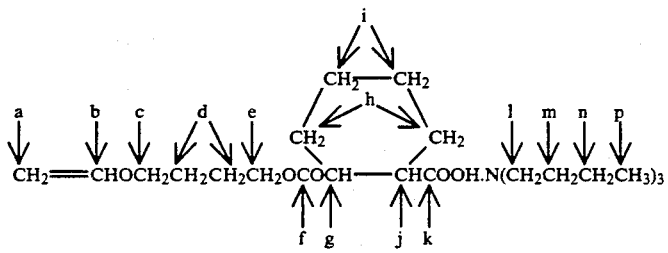

δ(ppm)=85.8 (a), 151.9 (b), 67.4 (c), 25.8-26.1 (d), 63.2 (e), 173.3 (f), 43.3 (g), 26.7 (h), 24.1-25.8 (i), 43.8 (j), 176.3 (k), 52.5 (l), 27.4 (m) 20.7 (n), 14.0 (p).
Yield: 100%

Example 8

Base: N-dimethylcyclohexylamine (127 g=1.0 mole) Vinyl ether (I) of the invention:

δ(ppm)=86.8 (a), 152.8 (b), 68.3 (c), 26.0-26.5 (d), 64.3 (e), 174.4 (f), 44.2 (g), 28.6 (h), 25.0-25.8 (i), 44.8 (j), 177.5 (k), 40.1 (l), 64.0 (m), 26.5-28.2 (n).
Yield: 100%

EXAMPLE 9

The vinyl ether (I) was prepared by repeating the same procedures as in Example 1 except that an amount of triethylamine was changed to an amount shown in Table 1. The yields determined by the FT-NMR analysis are shown in Table 1.

In addition, decomposition rates (%) of the resulting reaction products, when they were stored at ° C. and −20° C., were determined by $^{13}$C-NMR analysis. The results are also shown in Table 1.

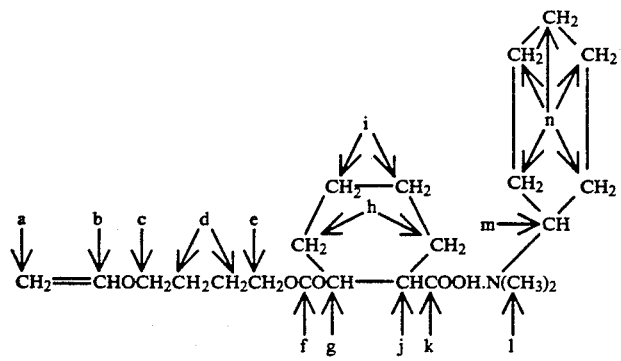

TABLE 1

| Experiment No. | Amount of triethylamine (% by mole to acid anhydride) | Yield of vinyl ethers | | | Decomposition rate (%) | |
| --- | --- | --- | --- | --- | --- | --- |
| | | (I) | (II) | (I) + (II) | 3 hrs after at 20° C. | 24 hrs after at −20° C. |
| 1 | 100 | 100 | — | 100 | 0 | 0 |
| 2 | 50 | 50 | 47 | 97 | 5 | 2 |
| 3 | 10 | 10 | 85 | 95 | 9 | 3 |
| 4 | 1 | 1 | 89 | 90 | 13 | 5 |

TABLE 1-continued

| Experiment No. | Amount of triethylamine (% by mole to acid anhydride) | Yield of vinyl ethers | | | Decomposition rate (%) | |
|---|---|---|---|---|---|---|
| | | (I) | (II) | (I) + (II) | 3 hrs after at 20° C. | 24 hrs after at −20° C. |
| 5 | 0.3 | 0.3 | 84.7 | 85 | 26 | 7 |
| Comparative Example 1 | 0 | 0 | 0 | 0 | — | — |

COMPARATIVE EXAMPLES 1

A flash of 1000 ml was charged with 154 g (1.0 mole) of 1,2-cyclohexanedicarboxylic anhydride and 40 g of acetone, and the mixture was stirred for 5 minutes with a magnetic stirrer.

To the mixture was added dropwise 116 g (1.0 mole) of hydroxybutyl vinyl ether at a rate of 2 g/min. while keeping the mixture at 0° to 10° C. by cooling with ice water.

As a result of analyzing the resulting reaction mixture by the FT-NMR analysis, there was not observed any signal of vinyl carbons, and the yielded product was an intramolecular ring closure compound of the formula:

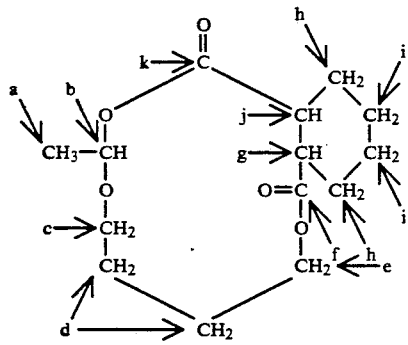

$\delta(ppm) = 19.5$ (a), 94.8 (b), 67.1 (c), 25.0–25.2 (d), 62.8 (e), 171.6 (f), 41.4 (g), 24.3–24.6 (h,i), 41.5 (j), 171.7 (k).

EXAMPLE 10

To the reaction product obtained in Experiment No. 5 of Example 9 (vinyl ether (I)/(II)=0.3/84.7 molar ratio) was added the base shown in Table 2 to convert the vinyl ether (II) into the vinyl ether (I). Decomposition rates of the resulting products were determined in the same manner as in Example 9. The results are shown in Table 2.

TABLE 2

| Experiment No. | Base 3 | | | Decomposition rate (%) | |
|---|---|---|---|---|---|
| | Kind | Molar ratio to vinyl ether (II) | pKa | 3 hrs after at 20° C. | 24 hrs after at −20° C. |
| 6 | Sodium hydroxide | 1.0 | — | 0 | 0 |
| 7 | Ammonia | 1.0 | 9.25 | 0 | 0 |
| 8 | Triethanolamine | 1.0 | 7.762 | 0 | 0 |
| 9 | Tributylphosphine | 1.0 | 8.4 | 0 | 0 |
| 10 | Pyridine | 1.0 | 5.22 | 21 | 8 |
| 11 | Dimethylformamide | 1.0 | <6 | 18 | 6 |
| 12 | Aniline | 1.0 | 4.596 | 20 | 7 |

As is clear from Table 2, the basic compounds having a pKa of lower than 6 less contribute to stability of the vinyl ethers (II) due to their weak base.

EXAMPLE 11

A glass autoclave of 1000 ml with a stirrer was charged with 145 g of diglyme, 175 g of isopropylalcohol (hereinafter referred to as "IPA"), 63 g (0.23 mole) of the compound (a) of the formula:

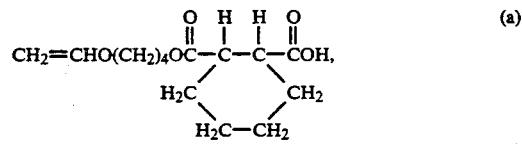

9.6 g (0.026 mole) of the compound (b) of the formula:

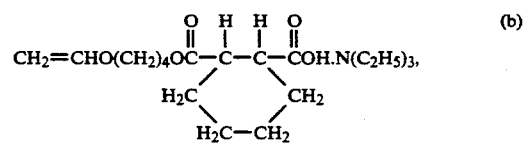

78 g g (0.39 mole) of vinyl ester of carboxylic acid having a $C_{10}$ alkyl group (VEOVA ® 10 available from Shell Chemical, Co.; hereinafter referred to as "VA") and 62 g (0.53 mole) of hydroxybutyl vinyl ether hereinafter referred to as "HBVE"). After deaeration, 140 g g (1.20 mole) of chlorotrifluoroethylene was added to the mixture. The autoclave was heated with stirring at 300 rpm and, when a temperature of the mixture reached to 65° C., 3.2 g of azobisisobutyronitrile (hereinafter referred to as "AIBN") dissolved in 30 g of diglyme was introduced under a nitrogen gas pressure. At that time, an inner pressure of the autoclave was 8.2 kg/cm²G.

The mixture was continuously stirred until the inner pressure was decreased to 1.0 kg/cm²G at the same temperature (for about 12 hours), and the autoclave was cooled to room temperature with water, and then the gas phase in the autoclave was replaced by nitrogen gas. The resulting reaction mixture contained a copolymer in a concentration of 48% by weight (copolymer yield: 336 g).

The reaction mixture was thrown into a petroleum benzine, and the precipitate (copolymer) was washed and dried. As a result of elementary analysis, IR analysis and NMR analysis, the copolymer consisted of CTFE (50.5% by mole), the vinyl ethers (I) and (II) (sum of them being 11.0% by mole), HBVE (22.5% by mole)

and VA (16.0% by mole). The number average molecular weight ($\overline{Mn}$) measured by GPC was 25,000.

EXAMPLE 12 TO 25 AND COMPARATIVE EXAMPLES 2 TO 4

The same procedures as in Example 11 were repeated except that the monomer,.s, solvents and initiating agents (and their weight ratio) shown in Table 3 were used to give copolymers.

In Table 3, yielded amount, yields and $\overline{Mn}$ of the copolymers are shown.

In Table 3, the abbreviations represent the following monomers (1), solvents (2) and initiating agents (3).

(1) Monomers:
TFE: Tetrafluoroethylene
VdF: Vinylidene fluoride
EVE: Ethyl vinyl ether
BVE: n-Buthyl vinyl ether
CHVE: Cyclohexyl vinyl ether
4FVE: 2,2,3,3-Tetrafluoropropyl vinyl ether
HBVE: Hydroxybutyl vinyl ether
M5FP: $CF_2=CFCF_2FH_2OH$

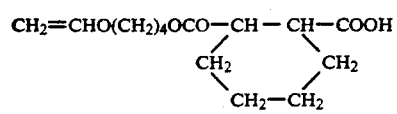  ①

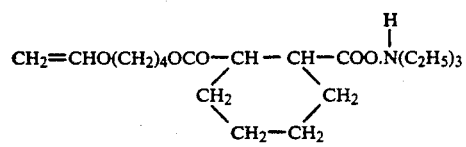  ②

$CH_2=CHO(CH_2)_4OCOCH_2CH_2COOH$  ③

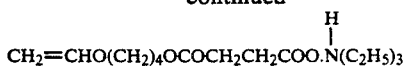  ④

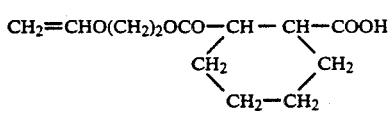  ⑤

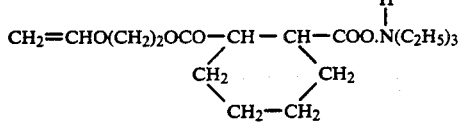  ⑥

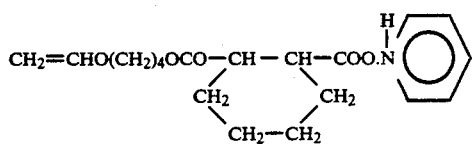  ⑦

(Experiment No. 10)

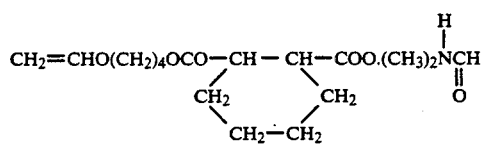  ⑧

(Experiment No. 11)

(2Solvents:
MIBK: Methyl isobutyl ketone
R-113: Trichlorotrifluoroethane
(b 3) Initating agents:
IPP: Diisopropyl peroxydicarbonate

TABLE 3

| Ex. No. | Monomers (g) | Solvents (g) | Initiating agent (g) | Temp. (°C.) | Time (hr) | Yielded amount (g) | Yield (%) | $\overline{Mn}$ |
|---|---|---|---|---|---|---|---|---|
| 12 | CTFE/①/② (105.5/228.2/25.4) | IPA/Diglyme (175.0/175.0) | AIBN (2.5) | 65 | 10.0 | 340.0 | 97.1 | 12,000 |
| 13 | CTFE/①/②/HBVE (131.7/142.3/15.8/65.6) | IPA/Diglyme (290.5/59.5) | AIBN (3.1) | 65 | 11.0 | 332.0 | 94.9 | 22,000 |
| 14 | CTFE/①/②/EVE (141.1/153.5/17.1/43.8) | Ethanol/Xylene (175.0/175.0) | AIBN (3.3) | 65 | 10.5 | 333.2 | 95.2 | 70,000 |
| 15 | CTFE/①/②/EVE/HBVE (161.9/77.0/8.6/33.0/72.5) | IPA/Diglyme (290.5/59.5) | AIBN (3.8) | 65 | 11.0 | 336.7 | 96.2 | 25,000 |
| 16 | CTFE/③/④/VA/HBVE (141.1/98.6/11.0/48.0/56.2) | IPA/Butyl cellosolve/ Diglyme (175.0/87.5/87.5) | AIBN (3.3) | 65 | 13.0 | 338.8 | 96.8 | 8,000 |
| 17 | CTFE/⑤/⑥/VA/HBVE (140.4/54.6/6.1/95.4/55.9) | IPA/Butyl cellosolve/ Diglyme (175.0/87.5/87.5) | AIBN (3.3) | 65 | 12.0 | 333.3 | 95.2 | 38,500 |
| 18 | CTFE/①/VA/HBVE (139.0/97.4/77.9/62.3) | IPA/Diglyme (175.0/175.0) | AIBN (3.2) | 65 | 13.0 | 328.3 | 93.8 | 46,000 |
| 19 | TFE/①/②/VA/HBVE (125.2/63.1/7.0/99.1/58.1) | IPA/Butyl cellosolve/ Diglyme (140.0/105.0/105.0) | AIBN (3.4) | 65 | 13.0 | 331.1 | 94.6 | 91,000 |
| 20 | CTFE/①/②/BVE/HBVE (160.7/69.6/7.7/82.8/32.0) | Ethanol/MIBK/Xylene (35.0/140.0/175.0) | AIBN (3.7) | 65 | 12.0 | 339.2 | 96.9 | 18,000 |
| 21 | CTFE/①/②/4FVE/HBVE (147.0/31.2/3.5/139.6/29.3) | Butyl/Ethyl/Butyl acetate/acetate/cellosolve (210.0/105.0/35.0) | AIBN (3.4) | 65 | 12.0 | 341.3 | 97.5 | 152,000 |
| 22 | CTFE/①/②/CHVE/HBVE (160.0/34.7/3.9/121.0/31.9) | Ethanol/MIBK/Xylene (35.0/35.0/280.0) | AIBN (3.7) | 65 | 12.0 | 342.3 | 97.8 | 88,000 |
| 23 | CTFE/VdF/①/②/M5FP (50.2/137.8/36.2/4.0/23.3) | R-113/Water (325.5/225.0) | IPP (4.9) | 40 | 20 | 234.3 | 93.7 | 29,000 |
| 24 | CTFE/② (105.5/313.6) | IPA/Diglyme (175.0/175.0) | AIBN (2.5) | 65 | 10.0 | 337.9 | 97.1 | 11,500 |
| 25 | CTFE/①/② (105.5/251.0/2.54) | IPA/Diglyme (175.0/175.0) | AIBN (2.5) | 65 | 10.0 | 319.0 | 91.1 | 9,800 |
| Comp. | CTFE/①/② | IPA/Diglyme | AIBN | 65 | 10.0 | 274.9 | 78.5 | 21,000 |

TABLE 3-continued

| Ex. No. | Monomers (g) | Solvents (g) | Initiating agent (g) | Temp. (°C.) | Time (hr) | Yielded amount (g) | Yield (%) | Mn |
|---|---|---|---|---|---|---|---|---|
| Ex. NO. 2 | (105.5/253.3/0.25) | (175.0/175.0) | (2.5) | | | | | |
| 3 | CTFE/⑦ (105.5/316.0) | IPA/Diglyme (175.0/175.0) | AIBN (2.5) | 65 | 10.0 | 86.8 | 24.8 | 5,800 |
| 4 | CTFE/⑧ (105.5/310.6) | IPA/Diglyme (175.0/175.0) | AIBN (2.5) | 65 | 10.0 | 224.7 | 64.2 | 8,900 |

What we claimed is:

1. Fluorine-containing copolymers prepared by copolymerizing fluoroolefins with vinyl ethers of the formula (I):

$$CH_2=CHOR^1OC(=O)R^2C(=O)O(H)_nM \quad (I)$$

wherein $R^1$ is a divalent aliphatic residue of 2 to 10 carbon atoms, $R^2$ is a divalent organic residue, and M is an alkali metal, or a mono-functional basic compound which contains nitorgen atom or phosphorus atom and has a pKa of 6 to 12, and n is O when M is the alkali metal, and is 1 when M is other, or monomer compositions of the vinyl ethers (I) and vinyl ethers of the formula (II):

$$CH_2=CHOR^1OC(=O)R^2C(=O)OH \quad (II)$$

wherein $R^1$ and $R^2$ are as defined above, and said monomer compositions containing the vinyl ethers (I) in an amount of not less than 1% by mole of the vinyl ethers (II).

2. The fluorine-containing copolymers of claim 1, wherein the monomer compositions contain the vinyl ethers (I) in an amount of not less than 5% by mole of the vinyl ethers (II).

3. The fluorine-containing copolymers of claim 1, wherein $R^2$ is a residue represented by the formula (i):

$$\pm(CHX^1)_p\pm(CX^2_2)_q \quad (i)$$

wherein $X^1$ is hydrogen atom or an alkyl group of 1 to 3 carbon atoms, $X^2$ is hydrogen atom or an alkyl group of 1 to 3 carbon atoms, and p and q are O or an integer of 1 to 11, provided that they are not O at the same time; a residue represented by the formula (ii):

$$\pm(CH_2)_r\pm(CX^3=CH)_s \quad (ii)$$

wherein $X^3$ is hydrogen atom or an alkyl group of 1 to 3 carbon atoms, r is O or an integer of 1 to 3, and s is an integar of 1 to 3; a residue represented by the formula (iii):

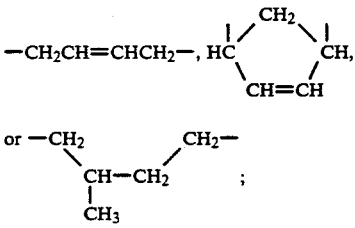

wherein $R^7$ is $\pm(CHX^4)_t$ in which $X^4$ is hydrogen atom or an alkyl group of 1 or 3 carbon atoms and t is an integar of 1 to 4,

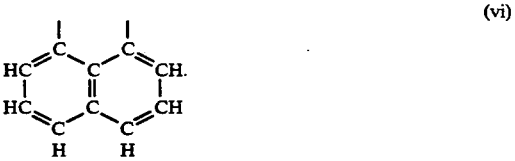

a residue represented by the formula (iv):

wherein $R^8$ is $\pm(CHX^5)_u$ in which $X^5$ is hydrogen atom or an alkyl group of 1 or 3 carbon atoms and u is an integar of 3 to 4, or $\pm(CX^6=CX^7)_v$ in which $X^6$ and $X^7$ are the same or different and each is hydrogen atom or an alkyl group of 1 to 3 carbon atoms and v is an integar of 2 to 3; a residue represented by the formula (v):

$$-C(=CH_2)-CH_2- \quad (v);$$

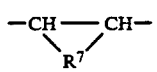

4. The fluorine-containing copolymers of claim 1, wherein the fluoroolefin is a member selected from the group consisting of tetrafluoroethylene, chlorotrifluoroethylene, hexafluoropropylene, trifluoroethylene, vinylidene fluoride and vinyl fluoride.

* * * * *